United States Patent
Sullivan et al.

(10) Patent No.: US 7,064,226 B2
(45) Date of Patent: Jun. 20, 2006

(54) ORGANOPOLYSILOXANES CONTAINING PHOSPHONIC GROUPS, METHOD FOR THE PRODUCTION AND USE THEREOF

(75) Inventors: Alice Caroline Sullivan, London (GB); John Robert Howe Wilson, London (GB)

(73) Assignee: PhosphonicS Limited, London (GB)

( * ) Notice: Subject to any disclaimer, the term of this patent is extended or adjusted under 35 U.S.C. 154(b) by 0 days.

(21) Appl. No.: 10/250,732

(22) PCT Filed: Jan. 9, 2002

(86) PCT No.: PCT/GB02/00069

§ 371 (c)(1),
(2), (4) Date: Nov. 21, 2003

(87) PCT Pub. No.: WO02/055587

PCT Pub. Date: Jul. 18, 2002

(65) Prior Publication Data

US 2004/0077889 A1  Apr. 22, 2004

(30) Foreign Application Priority Data

Jan. 9, 2001 (GB) .................................. 0100470.4

(51) Int. Cl.
*C07F 9/02* (2006.01)
(52) U.S. Cl. ..................................... 556/404
(58) Field of Classification Search ................. 556/13, 556/404
See application file for complete search history.

(56) References Cited

U.S. PATENT DOCUMENTS

| | | | | |
|---|---|---|---|---|
| 3,546,179 A | * | 12/1970 | Kolier | 528/275 |
| 3,816,550 A | * | 6/1974 | Young | 568/898 |
| 4,002,427 A | * | 1/1977 | Moller et al. | 8/155.1 |
| 4,617,344 A | * | 10/1986 | Tanaka et al. | 524/837 |
| 5,627,296 A | * | 5/1997 | Dauth et al. | 556/405 |

FOREIGN PATENT DOCUMENTS

| | | | |
|---|---|---|---|
| EP | 0525573 | | 2/1993 |
| EP | 0744432 | | 11/1996 |
| FR | 2189463 | | 1/1974 |
| GB | 836241 | * | 6/1960 |
| GB | 836241 | | 6/1990 |
| SU | 523911 | | 8/1976 |

\* cited by examiner

OTHER PUBLICATIONS

Dolgov et al., Telomerization of Dialkyl Phosphites and Bis(Trialkylsilly) Phosphites with Vinylsilane Derivatives, Translated from Zhurnal Obshchei Khimii, vol. 40, No. 7, pp. 1668-1669, Jul. 1970.*

Primary Examiner—Johann Richter
Assistant Examiner—Chukwuma Nwaonicha
(74) Attorney, Agent, or Firm—Evelyn H. McConathy; Drinker, Biddle & Reath LLP

(57) ABSTRACT

The invention relates to new compounds of the formula, wherein R and $R^1$ are each independently hydrogen, a linear or branched $C_{1-40}$ alkyl, $C_{2-40}$ alkenyl or $C_{2-40}$ alkynyl group, an aryl or $C_{1-40}$ alkylaryl group or an optionally complex metal ion $M^{n+}/n$ wherein n is an integer from 1 to 8; the free valences of the silicate oxygen atoms are saturated by one or more of: silicon atoms of other groups of the formula, hydrogen, a linear or branched $C_{1-12}$ alkyl group or by cross-linking bridge members $R^3_q M^1(OR^2)_m O_{k/2}$ or $Al(OR^2)_{3-p}O_{p/2}$ or $R^3 Al(OR^2)_{2-r}O_{r/2}$; where $M^1$ is Si or Ti; $R^2$ is linear or branched $C_{1-12}$ alkyl group; and $R^3$ is a linear or branched $C_{1-6}$ alkyl group; k is an integer from 1 to 4 and q and m are integers from 0 to 2; such that $m+k+q=4$; and p is an integer from 1 to 3; and r is an integer from 1 to 2; or other known oxo metal bridging systems; x, y and z are integers such that the radio of x:y+z, varies from 0.00001 to 100,000 with the fragments $[O_{3/2}SiCH(CH_2PO(OR)(OR^1))CH_2CH_2SiO_{3/2}]_X$ and $[O_{3/2}SiCH_2CH_2PO(OR)(OR^1)]_Y$ always present whilst the integer z varies from 0 to 200y. The compounds are useful as catalysts for a wide variety of reactions and have the advantages that they can be prepared in a one-pot reaction and have functional group losding can be tailored to be at a required level. In addition, the compounds have high chemical and thermal stability, fixed and rigid structures, are insoluble in organic solvents, high resistance to ageing, and can easily be purified and reused.

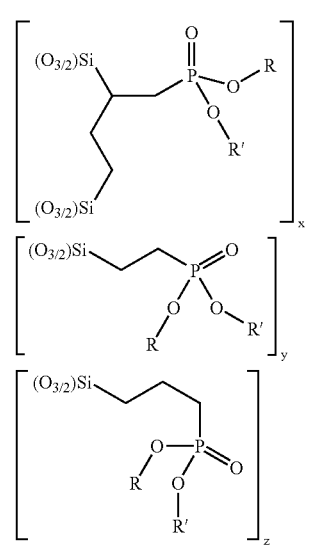

(1)

49 Claims, No Drawings

ORGANOPOLYSILOXANES CONTAINING PHOSPHONIC GROUPS, METHOD FOR THE PRODUCTION AND USE THEREOF

BACKGROUND OF THE INVENTION

The invention relates to new organopolysiloxanes containing phosphonic acid groups which can act as acid catalysts, cation exchangers and possess in their characteristics a number of advantages over organic polymer systems and inorganic supporting materials. In addition the metal salts of the organopolysiloxane phosphonic acids can be used to catalyse a wide variety of chemical transformations. Precursors of these new products, processes for their production and their uses are also described.

As is known, acid catalysts are utilised in the chemical and biochemical industry to conduct a wide range of chemical transformations. A range of homogenous and heterogeneous catalysts are used some of which require high temperatures to be effective and some produce considerable amount of bi-products and waste. These unwanted products and waste have to be treated and destroyed. The drive for more environmentally friendly processes—Green Chemistry—highlights the need for reusable, more effective and selective catalysts. This need has led to investigations into the design of new materials which can catalyse a variety of chemical transformations. Key requirements for such new catalysts are very good thermal stability, high insensitivity to chemical attack, high functional group loading, fixed and rigid structures, optimum functional groups so as to avoid rearrangements and side products, limited swelling capability, insolubility in organic solvents, ease of purification and high reusability, high ageing resistance and ease of access to the functional group which conducts the chemical transformation. In addition the processes to make such catalyst systems have to be flexible so as to enable the production of optimum structures and shapes for specific reactions. This could include tailoring the porosity from anywhere between macroporous to microporous structures, variable loading of the functional group, ease of making different metal derivatives and selective pH ranges.

A range of metals and catalysts have been embedded within or adsorbed on to the surface of silica, and other materials. The state of this art, for silica and its derivatives, is described by M. A. Brook in Silicon in Organic, Organometallic and Polymer Chemistry, Chapter 10, page 318, John Wiley & Sons, Inc., 2000. One of the problems encountered with these systems is the loss of the active functional groups due to their often very weak attachment to the silica New organo-silica materials are needed which whilst possessing the properties described above have functional groups which are strongly attached and which bind strongly to a range of metals and catalysts.

As a consequence of stricter environmental regulations there is a growing requirement for more effective systems for the removal and recovery of metals from a wide spectrum of metal contaminated solvents and aqueous based wastes and from contaminated waters. For example industries such as the nuclear industry and the electroplating industry generate substantial quantities of water-based effluent which are heavily contaminated with undesirable metal ions. Cation exchangers have been used to remove metal ions from solution and the state of this art is described in Kirk—Othmer's Encyclopaedia of Chemical Technology, 4th Edition, Vol. 14, page 737. The type of cation exchangers which are employed consist primarily of an organic, partly cross-linked polystyrene backbone with sulfonate groups attached to some of the phenyl rings. The physical and chemical properties of these polystyrene sulfonic cation exchangers are strongly affected by the organic nature of the polymeric backbone so that a number of disadvantages affect their technical field of application. The chemical and physical properties of a variety of such polystyrene based systems are described in the Bio-Rad Life Science Research Products catalogue 1998/99, pages 56–64. These limitations include relatively low temperature resistance 100°–130° C., sensitivity to chemical attack which can result in complete breakdown of the polymer matrix, strong swelling capacity, non-usability in certain organic solvents and the need for swelling to make the functional groups accessible. Organophosphonic acid cation exchangers have also been reported in U.S. Pat. No. 5,281,631. These systems are based on the products from the copolymerisation of the very expensive vinylidene disphosphonic acid with styrene, acrylonitrile and divinylbenzene. However the physical and chemical properties of these organophosphonic acid resins are very similar to the polystyrene sulfonic acid based systems and thus likewise their field of application is limited.

Inorganic polymer systems such as silica, aluminium oxide and titanium oxide, which do not suffer some of these drawbacks, have been investigated as ion exchangers. Active functional groups or metals are attached by a variety of means to these systems. However these systems suffer from the fact that only a low level of functional groups can be bound onto these surfaces. One of the additional problems encountered with these systems is that the functional groups can be removed on use or on standing. This is due to the rather weak attachment between the functional group and the surface atoms on the support.

Strong acidic cation exchangers based on sulfonic acid groups attached to a organopolysiloxane backbone have been described in U.S. Pat. No. 4,552,700 and U.S. Pat. No. 5,354,831. The materials reported have a general formula of $(O_{3/2}Si—R^1—SO_3^-)_xM^x$ where $R^1$ is an alkyl or cycloalkyl fragment, M is hydrogen or a mono to tetravalent metal ion and where the free valences of the oxygen atoms being saturated by silicon atoms of other groups of this formula and/or by cross-linking bridge members such as $SiO_{4/2}$, $R^1SiO_{3/2}$, $TiO_{4/2}$, $AlO_{3/2}$, etc. Whilst these materials can act as cation exchangers it is generally recognised that sulfonic acid groups are limited in their effectiveness to complex with a range of metals and in comparison to other functional groups. In addition the sulfonate group is also limited by the fact that it is a mono anion and thus more of these functional groups are needed to bind to metals compared to other functional groups.

DESCRIPTION OF PREFERRED EMBODIMENTS OF THE INVENTION

The present invention relates to novel compounds which are capable of acting as catalysts, catalyst immobilisation supports and ion exchanger materials, or which are precursors for these. Therefore, in a first aspect of the present invention, there is provided a compound of General Formula 1:

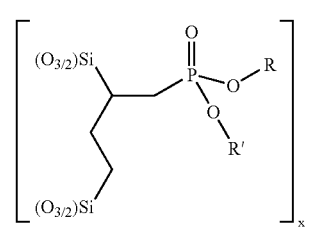

Formula 1

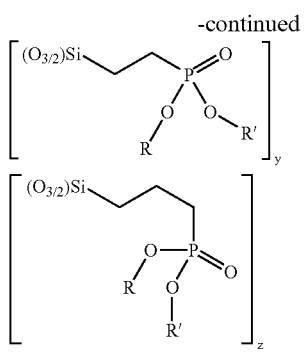

wherein R and $R^1$ are each independently hydrogen, a linear or branched $C_{1-40}$ alkyl, $C_{2-40}$ alkenyl or $C_{2-40}$ alkynyl group, an aryl or $C_{1-40}$ alkylaryl group or an optionally complex metal ion $M^{n+}/n$ wherein n is an integer from 1 to 8;

the free valences of the silicate oxygen atoms are saturated by one or more of:

silicon atoms of other groups of Formula 1, hydrogen, a linear or branched $C_{1-12}$ alkyl group or by cross-linking bridge members $R^3{}_qM^1(OR^2)_mO_{k/2}$ or $Al(OR^2)_{3-p}O_{p/2}$ or $R^3Al(OR^2)_{2-r}O_{r/2}$;

where $M^1$ is Si or Ti;

$R^2$ is a linear or branched $C_{1-12}$ alkyl group; and $R^3$ is a linear or branched $C_{1-6}$ alkyl group;

k is an integer from 1 to 4 and q and m are integers from 0 to 2;

such that m+k+q=4; and p is an integer from 1 to 3; and r is an integer from 1 to 2;

or other known oxo metal bridging systems;

x, y and z are integers such that the ratio of x:y+z, varies from 0.00001 to 100,000 with the fragments $[O_{3/2}SiCH(CH_2PO(OR)(OR^1))CH_2CH_2SiO_{3/2}]_x$ and $[O_{3/2}SiCH_2CH_2PO(OR)(OR^1)]_y$ always present whilst the integer z varies from 0 to 200y.

General Formula 1 can be abbreviated to $X_xY_yZ_z$ where X represents $[O_{3/2}SiCH(CH_2PO(OR)(OR^1))CH_2CH_2SiO_{3/2}]$, Y represents $[O_{3/2}SiCH_2CH_2PO(OR)(OR^1)]$ and Z represents $[O_{3/2}SiCH_2CH_2CH_2PO(OR)(OR^1)]$.

One advantage of the new catalysts, catalyst immobilisation supports and cation exchangers based on compounds of Formula 1 is that the functional group which can be selected to have either a high or a low value according to the requirements of the user. Other advantages include high thermal stability, fixed and rigid structures, good stability to a wide range of chemical conditions, insolubility in organic solvents, high resistance to ageing, easily purified and high reusability. In addition the processes for the preparation of compounds of Formula 1 are very flexible, enabling the porosity to be varied from micro to macro porous, the loading of the phosphonic acid to be varied as required and a wide range of metal derivatives to be made with the added advantage of a high metal incorporation. Furthermore compounds of Formula 1 have the added advantages of a more effective cation exchange group compared to sulfonate, of strong metal to phosphonate binding and thus little or no leaching on operation, and a mild and selective acid catalyst over a broad pH range.

The organopolysiloxanes containing sulfonic acids described in U.S. Pat. No. 4,552,700 require the presence of cross-linking agents containing Si, Ti or Al to provide the desired stability. Unlike these systems, compounds of Formula 1 do not require these cross linking agents to possess the desired physical and chemical properties. The bridging unit $[O_{3/2}SiCH(CH_2PO(OR)(OR^1))CH_2CH_2SiO_{3/2}]$ in Formula 1 provides the necessary cross-linking.

In the context of the present invention, $C_{1-40}$ alkyl refers to a straight, branched or cyclic hydrocarbon chain having from one to forty carbon atoms. The $C_{1-40}$ alkyl group may be substituted with one or more substituents selected from nitro, chloro, fluoro, bromo, nitrile, $C_{1-6}$ alkoxy, amino, amino $C_{1-40}$ alkyl or amino di($C_{1-40}$ alkyl). Examples include methyl, ethyl, isopropyl, n-propyl, butyl, t-butyl, n-hexyl, n-decyl, n-dodecyl, cyclohexyl, octyl, iso-octyl, hexadecyl, octadecyl, iso-octadecyl and docosyl. A $C_{1-12}$ alkyl group has from one to twelve carbon atoms.

In the context of the present invention, $C_{2-40}$ alkenyl refers to a straight, branched or cyclic hydrocarbon chain having from one to forty carbon atoms and including at least one carbon-carbon double bond. The $C_{2-40}$ alkenyl group may be substituted with one or more substituents selected from nitro, chloro, fluoro, bromo, nitrile, $C_{1-6}$ alkoxy, amino, amino $C_{1-40}$ alkyl or amino di($C_{1-40}$ alkyl). Examples include ethenyl, 2-propenyl, cyclohexenyl, octenyl, iso-octenyl, hexadecenyl, octadecenyl, iso-octadecenyl and docosenyl.

In the context of the present invention, $C_{2-40}$ alkynyl refers to a straight, branched or cyclic hydrocarbon chain having from one to forty carbon atoms and including at least one carbon-carbon triple bond. The $C_{2-40}$ alkynyl group may be substituted with one or more substituents selected from nitro, chloro, fluoro, bromo, nitrile, $C_{1-6}$ alkoxy, amino, amino $C_{1-40}$ alkyl or amino di($C_{1-40}$ alkyl). Examples include ethynyl, 2-propynyl octynyl, iso-octynyl, hexadecynyl, octadecynyl, iso-octadecynyl and docosynyl.

$C_{1-6}$ alkoxy refers to a straight or branched hydrocarbon chain having from one to six carbon atoms and attached to an oxygen atom. Examples include methoxy, ethoxy, propoxy, t-butoxy and n-butoxy.

The term aryl refers to a five or six membered cyclic, 8–10 membered bicyclic or 10–13 membered tricyclic group with aromatic character and includes systems which contain one or more heteroatoms, for example, N, O or S. The aryl group may be substituted with one or more substituents selected from nitro, chloro, fluoro, bromo, nitrile, $C_{1-6}$ alkoxy, amino, amino $C_{1-40}$ alkyl or amino di($C_{1-40}$ alkyl). Examples include phenyl, pyridinyl and furanyl.

The term $C_{1-40}$ alkylaryl group refers to a straight or branched hydrocarbon chain having from one to forty carbon atoms linked to an aryl group. The $C_{1-40}$ alkylaryl group may be substituted with one or more substituents selected from nitro, chloro, fluoro, bromo, nitrile, $C_{1-6}$ alkoxy, amino, amino $C_{1-40}$ alkyl or amino di($C_{1-40}$ alkyl). Examples include benzyl, phenylethyl and pyridylmethyl. In a $C_{1-8}$ alkylaryl group, the alkyl chain has from one to eight carbon atoms In the compounds of Formula 1 which are catalyst precursors, it is preferred that R and $R^1$ are each independently hydrogen, $C_{1-12}$ alkyl, $C_{2-12}$ alkenyl, $C_{2-12}$ alkynyl, aryl or $C_{1-8}$ alkylaryl.

Compounds in which R and $R^1$ are each independently hydrogen, $C_{1-4}$ alkyl, phenyl or $C_{1-8}$ alkylaryl are especially preferred.

Among the most useful precursor compounds of Formula 1 are those in which R and $R^1$ are each independently hydrogen, methyl, ethyl or phenyl.

Compounds of Formula 1 in which either or both R and $R^1$ are hydrogen have been found to be useful for catalysing a wide range of reactions, particularly reactions which are conventionally acid catalysed such as condensation reactions of aldehydes and ketones, ketalisation and acetalisation reactions, dehydration of olefins, a wide range of rearrangement and fragmentation reactions, isomerisations, esterifications and the trans-esterification of carboxylate esters.

If only one of R and $R^1$ is hydrogen, the other may be $C_{1-40}$ alkyl, $C_{2-40}$ alkenyl, $C_{2-40}$ alkynyl, aryl, $C_{1-8}$ alkylaryl or a metal ion derived from a lanthanide, actinide, main group or transition metal.

It is preferred that the R or group which is not hydrogen is $C_{1-4}$ alkyl, phenyl, $C_{1-8}$ aralkyl, particularly methyl, ethyl or phenyl.

Compounds of Formula 1 in which either or both of R and $R^1$ are $M^{n+}/n$ are particularly useful as solid immobilisation supports for metal catalysts and complexes and as heterogeneous catalysts for a wide range of reactions, for example oxidations, reductions, alkylations, polymerisations, hydroformylations, arylations, acylations, isomerisations, alkylations, carboxylations, carbonylations, esterifications, trans-esterifications and rearrangements.

In these compounds, if only one of R and $R^1$ is $M^{n+}/n$, it is preferred that the other of R and $R^1$ is hydrogen or a $C_{1-12}$ alkyl, $C_{1-12}$ alkenyl, $C_{1-12}$ alkynyl aryl or $C_{1-8}$ alkylaryl.

Preferred $M^{n+}$ are ions derived from lanthanide, actinide, main group or transition metals and more preferred $M^{n+}$ ions are derived from lanthanide, main group or transition metals.

The metal salts of Formula 1 are also useful as cation exchangers and preferred R, $R^1$ and $M^{n+}$ are as specified above.

For applications such as asymmetric synthesis, a chiral compound of Formula 1 may be required, in this case, it is preferred that one of R and $R^1$ is hydrogen or $M^{n+}/n$ and that the other is $C_{12-40}$ alkyl, $C_{12-40}$ alkenyl, $C_{12-40}$ alkynyl, $C_{12-40}$ alkylaryl or aryl.

Suitable alkyl, alkenyl and alkynyl groups for this type of synthesis are well known. Preferred $M^{n+}$ are as described above.

Where a cross linker is used, it is preferred that the ratio of cross linker to x+y+z varies from 0 to 99:1. Particularly suitable cross linkers are derived from orthosilicates, titanium alkoxides and alumninium trialkoxides. Examples include tetraethyl orthosilicate, aluminium triethoxide, aluminium tributoxide and titanium isopropoxide. The cross linking bridge member is preferably $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$. $R^2$ is preferably $C_{1-4}$ alkyl, most preferably methyl or ethyl.

It is particularly preferred that the ratio of x:y varies from 1:1000 to 1000:1 and more usually from 1:500 to 500:1.

Known sol-gel technology was used to produce the organopolysiloxane phosphonate esters of Formula 1 from monomeric precursors of Formula II, Formula m and Formula IV:

(R⁴O)₃SiCH₂CH₂PO(OR)(OR¹)    (II)

(R⁴O)₃SiCH₂CH₂CH₂PO(OR)(OR¹)    (III)

(R⁴O)₃SiCH(CH₂PO(OR)(OR¹))CH₂CH₂Si(OR⁴)₃    (IV)

R, $R^1$ and $R^4$ are $C_{1-12}$ alkyl, alkylaryl or aryl, preferably a methyl or ethyl group.

Compounds of Formulae II and III are known but compounds of Formula IV have not previously been reported.

The preparation of compounds of Formula 1 will now be discussed in greater detail. The general procedure used for the production of the organopolysiloxane phosphonate esters of Formula 1 consists of first forming the compounds (R⁴O)₃SiCH(CH₂PO(OR)(OR¹))CH₂CH₂Si(OR⁴)₃ (Formula IV) (R⁴O)₃SiCH₂CH₂PO(OR)(OR¹) (Formula II) and (R⁴O)₃SiCH₂CH₂CH₂PO(OR)(OR¹) (Formula III) and then combining them, in the desired ratios, in solvent with either dilute acid or base.

Compounds of Formula II can be synthesised via a free radical promoted addition of a dialkyl phosphite to vinyl trialkoxy silane and then distillation, according to the procedure of G. H. Barnes and M. P. David in *J. Org. Chem.*, 25, 1191, (1960). In this paper Barnes and David reported the synthesis of a number of organosilicon phosphonate esters and acids. They utilised known procedures for the free radical addition of dialkyl phosphites to double bonds. The state of this art is described in *Org. Reactions*. Vol. 13, 218–222. They reacted diethyl phosphite with vinyl triethoxy silane at 120–130° C. in the presence of a free radical initiator. The desired product, (EtO)₃SiCH₂CH₂PO(OEt)₂, was obtained after careful distillation in 33% yield.

Acid hydrolysis of (EtO)₃SiCH₂CH₂PO(OEt)₂ gave a reported formula of $[O_{3/2}SiCH_2CH_2PO(OH)_2]_m$ as a dry and brittle resin. The factor m can vary between four to ten. Repeating this work using the now preferred sol-gel technology afforded $[O_{3/2}SiCH_2CH_2PO(OEt)_2]_m$ as a viscous oil and subsequent hydrolysis gave $[O_{3/2}SiCH_2CH_2PO(OH)_2]_m$ as a very light and soft resin which did not possess the desired physical and chemical properties. The state of the arts of sol-gel technology and the hydrolysis of silicon esters are described by M. A. Brook in *Silicon in Organic, Organometallic and Polymer Chemistry* Chapter 10, page 318, John Wiley & Sons, Inc., 2000, G. A. Scherer in *Sol-gel science: the physcs and chemistry of sol-gel processing*, Boston: Academic Press, 1990, and J. D. Wright in *Sol-gel materials: chemistry and applications*, Amsterdam: Gordon and Breach Science Publishers, 2001 and the references contained within.

Compounds of Formula III can be prepared via an Arbuzov reaction between a trialkyl phosphite and 3-chloropropyltrialkoxysilane. The conditions for this reaction as described in JP 74,108,023 afford only a poor yield, less than 7% as determined by $^1H$ nmr spectroscopy, of the desired (R⁴O)₃SiCH₂CH₂CH₂PO(OR)(OR¹). However this compound was prepared in 70–90% yields by using sodium iodide as a catalyst and by heating between 160–170° C. for 48 hours as described in Example 5.

It is known that in general the free radical reaction between phosphorous acid or a dialkyl phosphite and an alkene does not proceed in high yield. Depending on the particular starting materials dimers and higher tellomers can be produced. The state of this art is described in *Org. Reactions*, Vol. 13, page 218–222 and the references provided therein. It was decided to use this general observation to produce organopolysiloxane comprising phosphonic groups with the desired physical and chemical properties.

Depending on the ratios of starting materials and temperature, varying ratios of (R⁴O)₃SiCH₂CH₂PO(OR)(OR¹) (Formula II) and (R⁴O)₃SiCH(CH₂PO(OR)(OR¹))CH₂CH₂Si(OR⁴)₃ (Formula IV) are produced via a free radical addition of dialkylphosphite to vinyl trialkoxy vinyl silane in the presence of a free radical initiator under an atmosphere of nitrogen. Diarylphosphites can also be used in this reaction. Particularly preferred are the cases where R, $R^1$ and $R^4$ are methyl or ethyl. A wide range of free radical initiators can be used for this reaction and preferred are the peroxides and in particular the alkyl peroxides. Addition of a very small amount of the initiator every few hours improves the overall yield. Reaction temperatures between 60° C. and 170° C. can be used, though a reaction temperature of between 100° C. and 140° C. is preferred. The presence of $(R^4O)_3SiCH(CH_2PO(OR)(OR^1))CH_2CH_2Si(OR^4)_3$ where R, $R^1$ and $R^4$=ethyl was identified by mass spectroscopy, m/e=518, using a Kratos MS50TC™ instrument and by comparison of its Si and P nuclear magnetic resonance spectra with related compounds. Although a wide range of solvents, well known to those skilled in the art of organic chemistry, can be used it is preferred to conduct this reaction without solvent. Reaction times of between 15 minutes to 48 hours have been used with 10 to 18 hours preferred. On completion of the reaction the unreacted starting materials are distilled off under reduced pressure and the resultant mixture is heated at between 100–120° C. at 1–2 mm of Hg. Heating at higher temperatures or at lower pressures will result in some of $(R^4O)_3SiCH_2CH_2PO(OR)(OR^1)$ (Formula II) where R, $R^1$ and $R^4$ are either methyl or ethyl distilling over. For example $(R^4O)_3SiCH_2CH_2PO(OR)(OR^1)$ where R, $R^1$ and $R^4$ are either methyl or ethyl can be obtained by distillation at 120° C. to 150° C. at pressures between 0.5–2 mm of Hg.

The ratios of $(R^4O)_3SiCH_2CH_2PO(OR)(OR^1)$ (Formula II) and $(R^4O)_3SiCH(CH_2PO(OR)(OR^1))CH_2CH_2Si(OR^4)_3$ (Formula IV) produced in the reaction can be varied by varying the ratio of dialkylphosphite to vinyl trialkoxy vinyl silane. For example a 2:1 ratio of dialkylphosphite to vinyl trialkoxy vinyl silane produces approximately a 3:1 ratio of $(R^4O)_3SiCH_2CH_2PO(OR)(OR^1)$ and $(R^4O)_3SiCH(CH_2PO(OR)(OR^1)CH_2CH_2Si(OR^4)_3$, where R, $R^1$ and $R^4$ are ethyl or methyl. A 1:1 ratio produces approximately a 3:2 ratio of $(R^4O)_3SiCH2CH_2PO(OR)(OR^1)$ (Formula II) and $((R^4O)_3SiCH(CH_2PO(OR)(OR^1))CH_2CH_2Si(OR^4)_3$ (Formula IV), where R, $R^1$ and $R^4$ are ethyl or methyl.

As already mentioned above, compounds of Formula IV, which are precursors of the bridging unit X: $[O_{3/2}SiCH(CH_2PO(OR)(OR^1))CH_2CH_2SiO_{3/2}]$ have not previously been reported.

Therefore, in a further aspect of the invention, there is provided a compound of Formula IV:

   (IV)

wherein R and $R^1$ and $R^4$ are each a linear or branched $C_{1-12}$ alkyl group, an aryl or alkylaryl group.

The invention also provides a process for the preparation of a compound of Formula IV as defined above, the process comprising the free radical addition of a dialkyl or diaryl phosphite of Formula VI:

   (VI)

where R is a linear or branched $C_{1-12}$ alkyl, aryl or $C_{1-12}$ alkylaryl group;

to trialkoxy vinyl silane of Formula V:

   (V)

where $R^4$ is a linear or branched $C_{1-12}$ alkyl, aryl or $C_{1-12}$ alkylaryl group; in the presence of a free radical initiator and under an atmosphere of nitrogen.

Compounds of Formulae II, III and IV are the precursors to compounds of Formula 1 and in a further aspect of the invention, there is provided a process for the preparation of a compound of Formula 1, the process comprising:
a. for a compound of Formula 1 in which R and $R^1$ are $C_{1-12}$ alkyl, alkylaryl or aryl:
  i. the free radical addition of a dialkyl or diaryl phosphite of Formula VI:

   (VI)

where R is a linear or branched $C_{1-12}$ alkyl, aryl or $C_{1-12}$ alkylaryl group;
  to trialkoxy vinyl silane of Formula V:

   (V)

where $R^4$ is a linear or branched $C_{1-12}$ alkyl, aryl or $C_{1-12}$ alkylaryl group; in the presence of a free radical initiator and under an atmosphere of nitrogen to give a mixture of compounds of Formulae II and IV;
  ii. combining, in the desired ratios, compounds of Formulae II, III and IV where R, $R^1$ and $R^4$ are $C_{1-12}$ alkyl, alkylaryl or aryl;
  iii. hydrolysing the mixture under acid or basic conditions; and optionally
  iv. adding a cross linking bridging precursor compound in a required quantity;
b. for a compound of Formula 1 in which R is hydrogen and $R^1$ is $C_{1-12}$ alkyl, alkylaryl or aryl:
  hydrolysing a compound of Formula 1 in which both R and $R^1$ are $C_{1-12}$ alkyl, alkylaryl or aryl under dilute acid or basic conditions; or
c. for a compound of Formula 1 in which R is hydrogen and $R^1$ is $C_{1-40}$ alkyl, $C_{2-40}$ alkenyl, $C_{2-40}$ alkynyl, aryl or alkylaryl:
  treating a compound of Formula 1 in which both R and $R^1$ are hydrogen with an acid chloride, concentrating the mixture and then reacting with a required alcohol $R^1OH$;
d. for a compound of Formula 1 in which R and $R^1$ are both hydrogen either:
  i. hydrolysing a compound of Formula 1 in which both R and $R^1$ are $C_{1-12}$ alkyl, alkylaryl or aryl in concentrated acid; or, when z=0
  ii. via free radical addition reaction between phosphorous acid of formula $H_3PO_3$ and a vinyl trialkoxysilane of Formula V:

   (V)

where $R^4$ is as defined above;
e. for a compound of Formula 1 in which R and/or $R^1$ is $M^{n+}/n$: reacting a compound of Formula 1 in which R and/or $R^1$ is hydrogen with base and then adding a solution containing the desired metal ion and/or complex.

Known sol-gel technology was used to produce the organopolysiloxane phosphonate esters of Formula 1 from the monomeric precursors of Formula II, Formula III and Formula IV. The state of the arts of sol-gel technology and the hydrolysis of silicon esters are described by M. A. Brook in *Silicon in Organic, Organometallic and Polymer Chemistry* Chapter 10, page 318, John Wiley & Sons, Inc., 2000, and the references contained within. Acids and bases were used to catalyse the hydrolysis of the silicon esters of Formula II, Formula III and Formula IV to produce the organopolysiloxane phosphonate esters of Formula 1.

A range of solvents, well known to those skilled in the art of organic chemistry, can be used to conduct this reaction. Alcohols are the preferred solvents particularly methanol and ethanol. After standing for a period of time the solution can be warmed to speed up the formation of the glass.

Ratios, by weight, of the alcohol solvent to the combined weight of the reagents from 100 to 0.01 can be used, with ranges from 2–10 being preferred. A range of acids can be used to aid hydrolysis with hydrochloric acid in concentrations ranging from 0.1 to 4 M being preferred. Hydrochloric acid, 1 molar, was routinely used. Ratios, from 0.000001 to 10, of hydrochloric acid, 1 molar, to the combined weight of the reagents can be used, with ranges from 0.0001 to 1 being preferred. In general the reaction mixture was left to stand at ambient temperature for 12 hours at temperatures ranging from 0° C.–120° C. to aid hydrolysis and the formation of the Si—O—Si bonds. Temperatures between 20° C.–60° C. are preferred and warming is continued until all the solvent has evaporated and a clear glass is obtained.

In addition to $(R^4O)_3SiCH(CH_2PO(OR)(OR^1))$ $CH_2CH_2Si(OR^4)_3$, (Formula IV) $(R^4O)_3SiCH_2CH_2PO(OR)(OR^1)$ (Formula II) and $(R^4O)_3SiCH_2CH_2CH_2PO(OR)(OR^1)$ Formula III), precursors to cross-linking bridge members such as $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is as defined above, but is preferably methyl or ethyl, or other oxo metals can be added in varying ratios to produce the desired compound of Formula 1.

These cross linking bridge precursors can be added at the same time as compounds of Formula II, III and IV. Suitable precursors include orthosilicates, titanium alkoxides and aluminium trialkoxides, for example tetraethyl orthosilicate, aluminium tributoxide, and titanium isopropoxide.

Templates to aid the preparation of pores with particular sizes and distributions in compounds of Formula 1 can be added at this stage. On preparation of the solid organopolysiloxane phosphonate esters of Formula 1 these templates can be washed out.

The organopolysiloxane phosphonate esters glasses of Formula 1 were broken up and ground to very fine particles prior to hydrolysis. Known crushing methods were used.

The monoesters of Formula 1, where R═H and $R^1$ is $C_{1-12}$ alkyl, alkylaryl or aryl are prepared by dilute basic or acidic hydrolysis of the corresponding phosphonate diesters of Formula 1. Bases such as sodium or potassium hydroxide in concentrations ranging from 0.1 to 20% by weight in water can be used with 1–5% preferred. Reaction temperatures of between 20–100° C. can be used with 30° C.–50° C. preferred. Reaction times for complete hydrolysis range from 1–48 h with 2–6 h preferred.

The organopolysiloxane phosphonic acids of Formula 1 where R and $R^1$ are hydrogen are prepared by direct hydrolysis, utilising the procedure of G. H. Barnes and M. P. David, *J. Org. Chem.*, 25, 1191, (1960), from the corresponding organopolysiloxane phosphonate esters of Formula 1. A ten-fold excess by volume or weight of concentrated hydrochloric acid to the organopolysiloxane phosphonate ester is used and the mixture is stirred under reflux for between 12–24 hours. After cooling the organopolysiloxane phosphonic acids are filtered off and washed with de-ionised water till the washings are pH 7. The solids are washed with ethanol and then ether and dried at between 20° C.–100° C. under reduced pressure 0.001–5 mm of Hg.

Compounds of Formula 1 where z=0 and R and $R^1$ are hydrogen can also be prepared via a free radical addition reaction between phosphorous acid and vinyl trialkoxysilane using free radical initiators. In general very little is known about this type of chemistry and the state of this art is described in *Org. Reactions*, Vol. 13, page 218–222 and the references provided therein. The reaction can be conducted with varying ratios, from 0.001–20 of phosphorous acid to vinyl trialkoxy silane with between 0.05–5 preferred. Methoxy and ethoxy are the preferred alkoxy groups.

A wide range of free radical initiators, well known to those skilled in the art of chemistry, can be used for this reaction and preferred are the peroxides and in particular the alkyl peroxides. Addition of very small amounts of the initiator every 1–3 hours improves the overall yield. Reaction temperatures between 60° C. and 170° C. can be used though a reaction temperature of between 100° C.–140° C. is preferred. On cooling the glass is washed well with de-ionised water to remove any un-reacted phosphorus acid and then crushed using known methods and then again washed well with de-ionised water. The solids are washed with ethanol and then ether and dried under reduced pressure, ranges between 20–100° C. and 0.001–5 mm of Hg can be used.

Differential Scanning Calorimetry (DSC) is a known technique for determining the thermal stability of compounds and materials. No thermal events were observed on heating any of the samples of Formula 1, prepared as described herein, up to a temperature of 400° C. under an atmosphere of nitrogen gas. A Perkin Elmer DSC 700™ instrument was used for these measurements. Thus compounds of Formula 1 possess very good thermal stability. A range of macro to micro porous materials of compounds of Formula 1 where R and $R^1$ are hydrogen were prepared.

The presence of both fragments X and Y in compounds of Formula 1 was evident from a detailed analysis of a series of $^1H$, $^{13}C$ and $^{31}P$ nmr experiments performed on the di-sodium salt of the compound from Example 1 conducted on a Bruker AMX 600™. For the fragment x the signals due to the methine carbon and its proton occur at $\delta_C$ 21.1 and $\delta_H$ 0.99 with the methylene carbon and its associated protons next to phosphorus are at $\delta_C$ 31.0 and $\delta_H$ 1.63 and 1.27. For the fragment y the signals due to the methylene carbon and its protons next to phosphorus occur at $\delta_C$ 22.6 and $\delta_H$ 1.36.

The mono esters of compounds of Formula 1 where R═H and $R^1$═$R^1$ is $C_{1-40}$ alkyl, $C_{2-40}$ alkenyl, $C_{2-40}$ alkynyl, aryl or alkylaryl were prepared by a two step procedure. Treatment of compounds of Formula 1 where R, $R^1$═H with an acid chloride followed by concentration and then reaction with an alcohol gave the mono esters of Formula 1. A range of acid chlorides, well known to the practitioners of organic chemistry can be used with thionyl chloride preferred. Using chiral alcohols optically active compounds of Formula 1 were prepared which can find application in asymmetric synthesis. The mono esters of compounds of Formula 1 where R═H and $R^1$=alkyl, aryl or alkylaryl were also prepared via hydrolysis using either acid or base in aqueous solvent mixtures. A range of acids and bases well known to the practitioners of organic chemistry can be used.

Compounds of Formula 1, where either or both of R and $R^1$ are hydrogen were found to catalyse a wide range of acid promoted reactions. In addition these compounds of Formula 1 possess good thermal and chemical stability. One of the advantages of these catalysts is that on completion of the reaction they can be simply filtered off and reused, without apparent loss of activity, in the same reaction without need for purification. No apparent loss of activity was observed. Following filtration and washing with solvents such as acetone, alcohols, water and others well known to those skilled in the art of organic chemistry and drying at temperatures ranging from 20° C.–120° C. under reduced pressure the compounds of Formula 1 can be used to catalyse other reaction types without apparent loss of activity.

These catalytic reactions can be conducted with or without solvent. The range of solvents which can be used include those well known to those skilled in organic and inorganic chemistry.

The following examples illustrate the catalytic activity of compounds of Formula 1 but are not intended to limit the scope of their capability to catalyse a wide range of reactions.

Compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C^{1-8}$ alkylaryl fragment, readily catalyse the condensation between aldehydes and aldehydes, aldehydes and ketones and ketones with ketones, reactions known as the Aldol condensation and the Claisen-Schmidt reaction. Standard conditions were used to conduct these reactions. For example heating under a Dean and Stark apparatus a 1:1 molar equivalent mixture of benzaldehyde and acetophenone in benzene or toluene in the presence of compounds of Formula 1 where R and $R^1$ are hydrogen gave the desired condensed product, 1,3-diphenyl prop-2-enone, in quantitative yield. An advantage of this procedure is that the catalyst can simply be filtered off and reused without any apparent reduction in activity. A range of compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment, successfully catalyse these transformations in very high yield.

Utilising known reaction conditions compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment, readily catalyse the ketalisation of ketones. Standard conditions were used to conduct these reactions. For example heating under a Dean and Stark apparatus acetophenone and an excess of ethylene glycol in benzene or toluene in the presence of compounds of Formula 1 where R and $R^1$ are hydrogen gave the desired product 2-methyl-2-phenyl-1,3-dioxolane in quantitative yield.

Utilising known reaction conditions compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment, readily catalyse the acetalisation of aldehydes. Standard conditions were used to conduct these reactions. For example treatment of benzaldehyde in methanol, with commonly used drying agents, in the presence of compounds of Formula 1 where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment gave the desired product 1,1-dimethoxy-1-phenyl methane in quantitative yield.

An advantage is that for both reactions, ketalisation and acetalisation, the catalyst can simply be filtered off and reused without any apparent reduction in activity. An additional advantage is that phosphonic acids are milder acids compared to the commonly used sulfonic acids for these reactions and are thus less likely to cause any rearrangements in the reactants or products.

Compounds of Formula 1 readily catalyse the dehydration of olefins. Standard conditions were used to conduct these reactions. For example heating cyclohexanol in the presence of compounds of Formula 1 where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment gave the desired cyclohexene. In a similar fashion treatment of 1-phenyl-1-propanol in toluene with catalysts of Formula 1 where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment in toluene at 75° C. gave β-methyl styrene in greater than 90% yield. An advantage of this procedure is that the catalyst can simply be filtered off and reused without any apparent reduction in activity.

Acids are widely used to catalyse a wide range of rearrangements and fragmentations. Likewise compounds of Formula 1 where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment readily catalyse a wide range of such reactions. For example heating 2,3-dimethyl butan-2,3-diol at between 130° C. to 180° C. without solvent in the presence of compounds of Formula 1 where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment gave 3,3-dimethyl butan-2-one in high yield. The reaction can also be conducted in a variety of solvents, well known to the practitioners of organic chemistry. Again the catalyst can simply be filtered off and reused without any apparent reduction in activity.

Heating 2,3-butanedione mono oxime at between 90–180° C. without solvent in the presence of compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment gave acetic acid and acetonitrile in high yield. The reaction can also be conducted in a variety of solvents, well known to practitioners in the art of chemistry. Again the catalyst can simply be filtered off and reused without any apparent reduction in activity.

Heating alkenes in the presence of compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment causes selective rearrangement. For example compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment catalyse the rearrangement of 1-octene to trans 2-octene. Again the catalyst can simply be filtered off and reused without any apparent reduction in activity.

The deketalisation and deacetalisation reactions are known to occur in the presence of aqueous acid. Compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment catalyse these transformations. For example stirring the ketal of acetophenone in the presence of compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment in an aqueous solvent mixture gave acetophenone in quantitative yield. An advantage of this procedure is that the catalyst can simply be filtered off and reused without any apparent reduction in activity.

Compounds of Formula 1 catalyse the esterification of carboxylic acids. For example treatment of oleic acid in refluxing ethanol with compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment gave the ester ethyl oleate in quantitative yield. An advantage of this procedure is that the catalyst can simply be filtered off and reused without any apparent reduction in activity.

Compounds of Formula 1 catalyse the trans-esterification of carboxylate esters. For example treatment of ethyl oleate in pentanol at temperatures between 60–140° C. with compounds of Formula 1, where R and $R^1$ are hydrogen or R is hydrogen and $R^1$ is a $C_{1-40}$ alkyl, $C_{2-40}$ alkenyl, $C_{2-40}$ alkynyl, aryl or $C_{1-8}$ alkylaryl fragment gave the ester pentyl oleate in quantitative yield. An advantage of this procedure is that the catalyst can simply be filtered off and reused without any apparent reduction in activity.

The monovalent to octavalent optionally complex metal ion salts of Formula 1 are prepared by first reacting the corresponding phosphonic acid derivatives of Formula 1 with dilute base to a pH of approximately 8–9. A solution containing the desired metal ion and/or complex is then added and the metal derivatives of Formula 1 are subsequently filtered off. A wide range of bases and solvents, well known to those skilled in the art of chemistry, can be used in this reaction with sodium or potassium hydroxide and water respectively preferred. The monovalent to octavalent optionally complex metal ion salts of Formula 1 can also be prepared in a range of non-aqueous solvents and by the use of appropriate bases and metal salts. In this manner a range of metal salts for example lanthanides, actinides, main group and transition metals of Formula 1 were prepared. Thus an important application of compounds of Formula 1 is their use as solid immobilisation supports for metal catalysts/complexes.

Metal salt/complexes of Formula 1 can catalyse a wide range of reactions well known to practitioners of organic and inorganic chemistry. Examples include but not limited to oxidations, reductions, alkylations, polymerisations, hydroformylations, arylations, acylations, isomerisations, alkylations, carboxylations, carbonylations, esterifications, transesterifications and rearrangements. These organopolysiloxane phosphonic systems of Formula 1 have many advantages for example they provide a support with very high thermal stability, good stability to a wide range of chemical conditions, a designable structure to facilitate selective reactions, and high loading of the active metal functional group. In addition these can be filtered off and reused. Thus an important application of the metal derivatives of Formula 1 is their use as heterogeneous catalysts.

The vanadyl metals salts of compounds of Formula 1 can be used to epoxidise a wide range of olefins. For example treatment of cis-cyclooctene with hydrogen peroxide in an aqueous—organic solvent mixture gave the corresponding epoxide in greater than 80% yield. A range of organic solvents, well known to practitioners or chemistry can be used in this reaction. The catalyst can simply be filtered off and reused without any apparent reduction in activity.

Cerium (IV) salts of compounds of Formula 1 can be used to oxidise a range of organic compounds. For example, alcohols, depending on their structure, can be oxidised to either ketones or carboxylic acids. Benzylic alcohols in the presence of cerium salts of Formula 1 and sodium bromate in an aqueous organic solvent mixture gave the corresponding benzoic acids in very high yield. In a similar fashion 2-octanol was oxidised to the ketone 2-octanone in 90% yield. A range of organic solvents, well known to practitioners or chemistry can be used in this reaction. The catalyst can simply be filtered off and reused without any apparent reduction in activity.

Cobalt salts of compounds of Formula 1 can be used for allylic oxidation. For example, treatment of the steroid pregnenolone acetate with a cobalt salt of formula 1 with an alkyl hydroperoxide in solvents such as acetonitrile and benzene gave the corresponding 5-ene-7-one derivative in 70% yield. The catalyst can simply be filtered off and reused without any apparent reduction in activity.

An important application of these new products is based on the ability of the polymeric organopolysiloxanes carrying phosphonate groups to exchange ions, that is to say, their application as a cation exchanger that can be used for all purposes and has the advantages of the matrix which is highly resistant to temperatures and solvents, of strongly fixed phosphonate groups which resist cleavage, of the resistance to swelling in aqueous and organic mediums, and their applicability in organic media also.

Therefore, another object of the invention is the use of the organopolysiloxanes that carry phosphonate groups as cation exchangers.

The new cation exchangers described herein can also be characterized with the aid of elementary analyses and their decomposition point exceeds 400° C. under protective gas atmosphere. The latter is evident from DSC analysis where no thermal events are seen below 400° C.

The mono and di-anion phosphonic derivatives of Formula 1 act as very effective cation exchangers for a wide range of metals of known oxidations state. These include the lanthanides, actinides, main group and transition metals.

The mono and di-anion phosphonic derivatives of Formula 1 are prepared by treatment with dilute base to pH 4 and pH 8 respectively. A range of bases and solvents, well known to those skilled in the art of chemistry, can be used such as aqueous metal hydroxides, alcoholic metal hydroxides, metal alkoxides and metal hydrides. Aqueous sodium or potassium hydroxide are the preferred bases for aqueous reactions. Fast and very effective cation exchange occurs following treatment of these derivatives with a wide variety of metal salts dissolved in various solvents. Numerous different analytical techniques, well known to those skilled in the art of chemistry, can be used to determine the extent of cation exchange.

For example eight grams of a disodium salt of Formula 1 can abstract 1.8 grams of $Co^{+2}$ from an aqueous environment. Treatment of this cobalt salt with acid regenerates the material which can be reused without apparent loss of activity.

In comparison a commercially available sulphonic acid resin, sold for use as a cation exchange resin, abstracts 0.12 grams of $Co^{+2}$ in a similar experiment.

Further applications of compounds of Formula 1 include the separation of amines, including optically active amines, the immobilisation of biological molecules such as enzymes and use as anti-microbial agents.

Therefore a further aspect of the invention provides an anti-microbial agent comprising a compound of Formula 1.

The invention will now be described in detail with reference to practical examples of the variants according to the invention, taking into account the starting materials that are fundamentally the most significant, but which are intended to be non-limiting.

EXAMPLE 1

A solution containing triethoxy vinyl silane (19.0 g, 0.136 mol), diethyl phosphite (19.32 g, 0.136 mol) and di-tertbutyl peroxide (6 drops) was heated at 120–130° C. under an atmosphere of nitrogen. Heating was continued for 40 h and di-tert butyl peroxide (6 drops) was added every 4 h. Un-reacted starting material was removed by heating at 120° C.—bath temperature—under reduced pressure (2 mm Hg) to give a mixture of diethyl 2,4di(triethoxysilyl)butylphosphonate and diethyl 2-triethoxysilyl ethylphosphonate as a colourless oil (30.1 g) in a ratio of 1.8:3.2.

The oil (30.1 g) was dissolved in methanol (125 ml) containing 1M HCl (10 ml). The solution was left at ambient temperature for 48 h and then at 55° C. for 100 h. The resultant glass (16.0 g) was crushed and then added to concentrated HCl (150 ml). The mixture was gently refluxed with stirring for 10 h and then cooled to room temperature.

The solid was filtered and first washed with distilled water till the washings were neutral and then with methanol and finally ether. After drying at 100° C. at 0.1 mm of Hg a pale white solid was obtained (13.0 g)—Catalyst A. DSC analysis—no thermal events were observed in heating a sample up to a temperature of 400° C. under an atmosphere of nitrogen gas.

Ester—Solid State MAS nmr; $\delta_P$ 32.83
Acid—Solid State MAS nmr; $\delta_P$ 30.93

EXAMPLE 2

A solution containing triethoxy vinyl silane (38.8 g, 0.204 mol), diethyl phosphite (28.17 g, 0.204 mol) and di tertbutyl peroxide (6 drops) was heated at 120–130° C. under an atmosphere of nitrogen. Heating was continued for 40 h and di-tert butyl peroxide (6 drops) was added every 4 h. Un-reacted starting material was removed by heating at 120° C.—bath temperature—under reduced pressure (2 mm Hg) to give a mixture of diethyl 2,4-di(triethoxysilyl)butylphosphonate and diethyl 2-triethoxysilyl ethylphosphonate as a colourless oil (55.1 g) in a ratio of 1.1:1.8.

The oil (55.1 g) was dissolved in methanol (200 ml) and then 1M HCl (20 ml) was added with stirring. The solution was left at ambient temperature for 48 h and then at 55° C. for 100 h. The resultant glass (30.0 g) was crushed and then added to concentrated HCl (300 ml). The mixture was gently refluxed with sting for 10 h and then cooled to room temperature. The solid was filtered and first washed with distilled water till the washings were neutral and then with methanol and finally ether. After drying at 100° C. at 0.1 mm of Hg a white solid (23.0 g)—Catalyst B—was obtained. DSC analysis—no thermal events were observed in heating a sample up to a temperature of 400° C. under an atmosphere of nitrogen gas.

EXAMPLE 3

A solution containing triethoxy vinyl silane (38.8 g, 0.204 mol), diethyl phosphite (42.25 g, 0.306 mol) and di-tertbutyl peroxide (6 drops) was heated at 120–130° C. under an atmosphere of nitrogen. Heating was continued for 40 h and di tert butyl peroxide (6 drops) was added every 4 h. Un-reacted starting material was removed by heating at 120° C.—bath temperature—under reduced pressure (2 mm Hg) to give a mixture of diethyl 2,4-di(triethoxysilyl)butylphosphonate and diethyl 2-triethoxysilyl ethylphosphonate as a colourless oil (58.6 g) in a ratio of 1:2.1.

The oil (58.6 g) was dissolved in methanol (230 ml) and then 1M HCl (25 ml) was added with stirring. The solution was left at ambient temperature for 4 h and then at 55° C. for 200 h. The resultant glass (32.0 g) was crushed and then added to concentrated HCl (305 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (25.0 g)—Catalyst C—was obtained. DSC analysis—no thermal events were observed in heating a sample up to a temperature of 400° C. under an atmosphere of nitrogen gas.

EXAMPLE 4

A solution containing triethoxy vinyl silane (19.4 g, 0.102 mol), diethyl phosphite (28.17 g, 0.204 mol) and di tertbutyl peroxide (6 drops) was heated at 120–130° C. under an atmosphere of nitrogen. Heating was continued for 40 h and di tert butyl peroxide (6 drops) was added every 4 h. Un-reacted starting material was removed by heating at 120° C.—bath temperature—under reduced pressure (2 mm Hg) to give a mixture of diethyl 2,4-di(triethoxysilyl)butylphosphonate and diethyl 2-triethoxysilyl ethylphosphonate as a colourless oil (28.3 g) in a ratio of 1:3.

The oil (28.3 g) was dissolved in methanol (120 ml) and then 1M HCl (15 ml) was added with stirring. The solution was left at ambient temperature for 2 h and then at 55° C. for 260 h. The resultant glass (20.1 g) was crushed and then added to concentrated HCl (100 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (15.0 g)—Catalyst D—was obtained. DSC analysis—no thermal events were observed in heating a sample up to a temperature of 400° C. under an atmosphere of nitrogen gas.

EXAMPLE 5

Preparation of Diethyl 3—triethoxysilyl propylphosphonate

A solution of 3-chloropropyl triethoxy silane (30 g, 0.125 m) and triethyl phosphite (20 ml, 0.125 mol) containing sodium iodide (0.1 g) was heated with stirring at 170–180° C.—bath temperature—for 40 h under an atmosphere of nitrogen. A $^1$H nmr of a sample of the reaction mixture indicated that the reaction had virtually gone to completion. The mixture was distilled under reduced pressure, 142° C. at 1 mm of Hg, to give diethyl 3—triethoxysilyl propylphosphonate (30 g, 70% yield).

EXAMPLE 6

A solution containing triethoxy vinyl silane (53.2 g, 0.306 mol), diethyl phosphite (21.2 g, 0.156 mol) and di tertbutyl peroxide (6 drops) was heated at 120–130° C. under an atmosphere of nitrogen. Heating was continued for 40 h and di tert butyl peroxide (6 drops) was added every 4 h. Un-reacted starting material was removed by heating at 120° C.—bath temperature—under reduced pressure (2 mm Hg) to give a mixture of diethyl 2,4-di(triethoxysilyl)butylphosphonate and diethyl 2-triethoxysilyl ethylphosphonate as a colourless oil (48.1 g).

The oil (48.1 g) was dissolved in methanol (240 ml) and then 1M HCl (18 ml) was added with stirring. The solution was left at ambient temperature for 48 h and then at 55° C. for 100 h. The resultant glass (33.0 g) was crushed and then added to concentrated HCl (290 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (24.0 g)—Catalyst E—was obtained. DSC analysis—no thermal events were observed in heating a sample up to a temperature of 400° C. under an atmosphere of nitrogen gas.

EXAMPLE 7

A mixture of diethyl 2,4-di-triethoxysilyl butylphosphonate and diethyl 2-triethoxysilyl ethylphosphonate (40 g, 1:5 ratio) was dissolved in methanol (150 ml) and then 1M HCl (12 ml) was added with stirring. The solution was left at ambient temperature for 4 h and then at 55° C. for 200 h. The resultant glass (22 g) was crushed and then added to concentrated HCl (200 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (16 g)—Catalyst F—was obtained. DSC analysis—no thermal events were observed in heating a sample up to a temperature of 400° C. under an atmosphere of nitrogen gas.

EXAMPLE 8

A mixture of diethyl 2,4-di triethoxysilyl butylphosphonate and diethyl 2-triethoxysilyl ethylphosphonate (35 g, 1:10 ratio) was dissolved in methanol (140 ml) and then 1M HCl (14 ml) was added with stirring. The solution was left at ambient temperature for 2 h and then at 55° C. for 260 h. The resultant glass (19 g) was crushed and then added to concentrated HCl (180 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (15.3 g)—Catalyst G—was obtained. DSC analysis—no thermal events were observed in heating a sample up to a temperature of 400° C. under an atmosphere of nitrogen gas.

EXAMPLE 9

A mixture of diethyl 2,4-di(triethoxysilyl)butylphosphonate and diethyl 2-triethoxysilyl ethylphosphonate (42 g, ratio 10:1) was dissolved in methanol (220 ml) and then 1M HCl (16 ml) was added with stirring. The solution was left at ambient temperature for 5 h and then at 55° C. for 300 h. The resultant glass (26.3 g) was crushed and then added to concentrated HCl (250 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (18.4 g) Catalyst H was obtained. DSC analysis—no thermal events were observed in heating a sample up to a temperature of 400° C. under an atmosphere of nitrogen gas.

EXAMPLE 10

A mixture of diethyl 2,4-di(triethoxysilyl)butylphosphonate and diethyl 2-triethoxysilyl ethylphosphonate (42 g, ratio 1:3) was dissolved in methanol (220 ml) and then 1M HCl (21 ml) was added with stirring. The solution was left at ambient temperature for 4 h and then at 55° C. for 300 h. The resultant glass (25.9 g) was crushed and then added to concentrated HCl (250 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (19.7 g)—Catalyst I— was obtained. DSC analysis—no thermal events were observed in heating a sample up to a temperature of 400° C. under an atmosphere of nitrogen gas.

Solid State MAS nmr $^{31}$P-$\delta_P$ 32.4

EXAMPLE 11

A mixture of diethyl 2,4-di(triethoxysilyl)butylphosphonate and diethyl 2-triethoxysilyl ethylphosphonate (5.8 g, ratio 1:2.5) and diethyl 3-triethoxysilylpropylphosphonate (1.0 g) was dissolved in methanol (25 ml) and then 1M HCl (2.5 ml) was added with stirring. The solution was left at ambient temperature for 4 h and then at 55° C. for 160 h. The resultant glass (4.7 g) was crushed and then added to concentrated HCl (47 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (3.9 g)—Catalyst J—was obtained. DSC analysis—no thermal events were observed in heating a sample up to a temperature of 400° C. under an atmosphere of nitrogen gas.

Solid State MAS nmr $^{31}$P-$\delta_P$ 32.4

EXAMPLE 12

A mixture of diethyl 2,4-di(triethoxysilyl)butylphosphonate and diethyl 2-triethoxysilyl ethylphosphonate (5.8 g, ratio 1:2.5) and diethyl 3-triethoxysilylpropylphosphonate (2 g) was dissolved in methanol (25 ml) and then 1M HCl (3 ml) was added with stirring. The solution was left at ambient temperature for 4 h and then at 55° C. for 200 h. The resultant glass (5.53 g) was crushed and then added to concentrated HCl (50 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (4.1 g)—Catalyst K—was obtained. DSC analysis—no thermal events were observed in heating a sample up to a temperature of 400° C. under an atmosphere of nitrogen gas.

Solid State MAS nmr $^{31}$P-$\delta_P$ 31.6

EXAMPLE 13

A mixture of diethyl 2,4-di(triethoxysilyl)butylphosphonate and diethyl 2-triethoxysilyl ethylphosphonate (42 g, ratio 1:3) and tetraethyl ortho silicate (6.0 g) was dissolved in methanol (220 ml) and then 1M HCl (16 ml) was added with stirring. The solution was left at ambient temperature for 4 h and then at 55° C. for 200 h. The resultant glass (27.2 g) was crushed and then added to concentrated HCl (250 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (18.3 g)—Catalyst L—was obtained. DSC analysis—no thermal events were observed in heating a sample up to a temperature of 400° C. under an atmosphere of nitrogen gas.

EXAMPLE 14

A mixture of diethyl 2,4-di(triethoxysilyl)butylphosphonate and diethyl 2-triethoxysilyl ethylphosphonate (5.8 g, ratio 1:0.5) and diethyl 3-triethoxysilylpropylphosphonate (8 g) was dissolved in methanol (55 ml) and then 1M HCl (4 ml) was added with stirring. The solution was left at ambient temperature for 4 h and then at 55° C. for 200 h. The resultant glass (9.5 g) was crushed and then added to concentrated HCl (90 ml). The mixture was gently refluxed with stirring for 10 h and then cooled to room temperature.

The solid was filtered and first washed with distilled water till the washings were neutral and then with methanol and finally ether. After drying at 100° C. at 0.1 mm of Hg a white solid (7.1 g)—Catalyst S—was obtained. DSC analysis—no thermal events were observed in heating a sample up to a temperature of 400° C. under an atmosphere of nitrogen gas.

EXAMPLE 15

A mixture of diethyl 2,4-di(triethoxysilyl)butylphosphonate and diethyl 2-triethoxysilyl ethylphosphonate (5.8 g, ratio 1:2.5) and diethyl 3-triethoxysilylpropylphosphonate (16 g) was dissolved in methanol (75 ml) and then 1M HCl (7 ml) was added with stirring. The solution was left at ambient temperature for 4 h and then at 55° C. for 200 h. The resultant glass (14.2 g) was crushed and then added to concentrated HCl (150 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (10.5 g)—Catalyst T—was obtained. DSC analysis—no thermal events were observed in heating a sample up to a temperature of 400° C. under an atmosphere of nitrogen gas.

EXAMPLE 16

A mixture of diethyl 2,4-di(triethoxysilyl)butylphosphonate and diethyl 2-triethoxysilyl ethylphosphonate (5.8 g, ratio 1:1) and diethyl 3-triethoxysilylpropylphosphonate (26 g) was dissolved in methanol (95 ml) and then 1M HCl (12 ml) was added with stirring. The solution was left at ambient temperature for 4 h and then at 55° C. for 200 h. The resultant glass (17.2 g) was crushed and then added to concentrated HCl (200 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (14.3 g)—Catalyst U—was obtained. DSC analysis—no thermal events were observed in heating a sample up to a temperature of 400° C. under an atmosphere of nitrogen gas

EXAMPLE 17

A solution containing trimethoxyvinyl silane (19.0 g, 0.136 mol), phosphorous acid (22.3 g, 0.27 mol) and di tertbutyl peroxide (6 drops) was heated at 120–130° C. under an atmosphere of nitrogen. Heating was continued for 12 h and di-tert butyl peroxide (6 drops) was added every 4 h. A colourless glass was obtained which was washed well with de-ionised water, crushed and then washed again with de-ionised water to afford a colourless solid (14.1 g)—Catalyst M.

EXAMPLE 18

A solution containing triethoxyvinyl silane (24.48 g, 0.136 mol), phosphorus acid (22.3 g, 0.27 mol) and di tertbutyl peroxide (6 drops) was heated at 120–130° C. under an atmosphere of nitrogen. Heating was continued for 12 h and di- tert butyl peroxide (6 drops) was added every 4 h. A colourless glass was obtained which was washed well with de-ionised water, crushed and then washed again with de-ionised water to a colourless solid (14.9 g)—Catalyst N.

EXAMPLE 19

A mixture of diethyl 2,4-di(triethoxysilyl)butylphosphonate and diethyl 2-triethoxysilyl ethylphosphonate (42 g, ratio 1:100) was dissolved in methanol (220 ml) and then 1M HCl (16 ml) was added with stirring. The solution was left at ambient temperature for 4 h and then at 55° C. for 300 h. The resultant glass (22.9 g) was crushed and then added to concentrated HCl (220 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (16.5 g)—Catalyst O—was obtained. DSC analysis—no thermal events were observed in heating a sample up to a temperature of 400° C. under an atmosphere of nitrogen gas.

EXAMPLE 20

A mixture of diethyl 2,4-di(triethoxysilyl)butylphosphonate and diethyl 2-triethoxysilyl ethylphosphonate (42 g, ratio 100:1) was dissolved in methanol (220 ml) and then 1M HCl (16 ml) was added with stirring. The solution was left at ambient temperature for 4 h and then at 55° C. for 300 h. The resultant glass (22.9 g) was crushed and then added to concentrated HCl (280 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (17.7 g)—Catalyst P—was obtained. DSC analysis—no thermal events were observed in heating a sample up to a temperature of 400° C. under an atmosphere of nitrogen gas.

EXAMPLE 21

A mixture of diethyl 2,4di(triethoxysilyl)butylphosphonate and diethyl 2-triethoxysilyl ethylphosphonate (42 g, ratio 1:50) was dissolved in methanol (220 ml) and then 1M HCl (16 ml) was added with stirring. The solution was left at ambient temperature for 4 h and then at 55° C. for 300 h. The resultant glass (18.8 g) was crushed and then added to concentrated HCl (200 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (13.8 g)—Catalyst Q—was obtained. DSC analysis— no thermal events were observed in heating a sample up to a temperature of 400° C. under an atmosphere of nitrogen gas.

EXAMPLE 22

A mixture of diethyl 2,4-di(triethoxysilyl)butylphosphonate and diethyl 2-triethoxysilyl ethylphosphonate (42 g, ratio 50:1) was dissolved in methanol (220 ml) and then 1M HCl (16 ml) was added with stirring. The solution was left at ambient temperature for 4 h and then at 55° C. for 300 h. The resultant glass (21.8 g) was crushed and then added to concentrated HCl (250 ml). The mixture was gently refluxed with stirring for 10 h and then cooled to room temperature. The solid was filtered and first washed with distilled water till the washings were neutral and then with methanol and finally ether. After drying at 100° C. at 0.1 mm of Hg a white solid (16.7 g)—Catalyst R—was obtained. DSC analysis—no thermal events were observed in heating a sample up to a temperature of 400° C. under an atmosphere of nitrogen gas.

EXAMPLE 23

A solution containing triethoxy vinyl silane (15.3 ml), diphenyl phosphite (19.15 ml) and di tert-butyl peroxide (6 drops) was heated at 120–130° C. under an atmosphere of nitrogen. Heating was continued for 40 h and di tert butyl peroxide (6 drops) was added every 4 h. The volatiles were removed by heating at 120° C.—bath temperature—under reduced pressure (2 mm Hg) to give a mixture of diphenyl 2,4-di(triethoxysilyl) butylphosphonate and diphenyl 2-triethoxysilyl ethylphosphonate as a colourless oil (30.3 g).

EXAMPLE 24

A mixture of diphenyl 2,4-di(triethoxysilyl)butylphosphonate and diphenyl 2-triethoxysilyl ethylphosphonate (8.0 g) was dissolved in methanol (30 ml) and then 1M HCl (2.5 ml) was added with stirring. The solution was left at ambient temperature for 4 h and then at 55° C. for 100 h. The resultant glass was crushed to give the diphenyl ester as a white solid (5.6 g).

EXAMPLE 25

A mixture of diphenyl 2,4-di(triethoxysilyl)butylphosphonate and diphenyl 2-triethoxysilyl ethylphosphonate (8.9 g) and tetraethyl ortho silicate (2.13 g) was dissolved in methanol (30 ml) and then 1M HCl (2.5 ml) was added with stirring. The solution was left at ambient temperature for 4 h and then at 55° C. for 100 h. The resultant glass was crushed to give the diphenyl ester as a white solid (6.6 g).

EXAMPLE 26

A mixture of diphenyl 2,4-di(triethoxysilyl)butylphosphonate and diphenyl 2-triethoxysilyl ethylphosphonate (8.13 g) and tetraethyl ortho silicate (4.12 g) was dissolved in methanol (30 ml) and then 1M HCl (2.5 ml) was added with stirring. The solution was left at ambient temperature for 4 h and then at 55° C. for 100 h. The resultant glass was crushed to give the diphenyl ester as a white solid (7.8 g).

EXAMPLE 27

A mixture of diphenyl 2,4-di(triethoxysilyl)butylphosphonate and diphenyl 2-triethoxysilyl ethylphosphonate (5.6 g) and tetraethyl ortho silicate (10.6 g) was dissolved in methanol (30 ml) and then 1M HCl (2.5 ml) was added with stirring. The solution was left at ambient temperature for 4 h and then at 55° C. for 100 h. The resultant glass was crushed to give the diphenyl ester as a white solid (7.2 g).

EXAMPLE 28

A mixture of diethyl 2,4-di(triethoxysilyl)butylphosphonate and diethyl 2-triethoxysilyl ethylphosphonate (6.1 g), tetraethyl ortho silicate (5.2 ml) and aluminium triethoxide (1.0 g) was stirred in methanol (40 ml) over a period of 2 h and then 1M HCl (2.5 ml) was added with stirring. The solution was left at ambient temperature for 4 h and then at 55° C. for 100 h. The resultant glass was crushed to give the diethyl ester as a white solid (6.57 g).

EXAMPLE 29

Sodium hydroxide (1M, 8 ml) was added to the crushed diester from Example 1 (0.4 g) suspended in ethanol (20 ml). The mixture was stirred and heated at 50° C. for 30 h then cooled to room temperature. After acidification with hydrochloric acid (1M) the mixture was concentrated to dryness under reduced pressure. Water (40 ml) was added and the solid was washed well with water and finally with ethanol and ether. A white light powdery solid (0.33 g) was obtained.

Solid State $^{31}$P MAS $\delta_P$ 31.994; $^{13}$C MAS $\delta_C$ 63.24, 34-8, 24.2, 10.52, 6.34

EXAMPLE 30

A mixture of Catalyst A (0.44 g) and thionyl chloride (5 ml) was stirred and heated under reflux for 1 h. After cooling to room temperature the excess thionyl chloride was removed under reduced pressure. Benzene (20 ml) was added to the residue and the mixture was stirred for 20 min then evaporated to dryness. This step was repeated three times. (R)-(–) 2-butanol (0.3 g) dissolved in dry benzene (10 ml) was added and the mixture was stirred at room temperature for 12 h. After concentrated to dryness under reduced pressure distilled water (20 ml) was added and the mixture was stirred at 80° C. for 4 h. On cooling the white solid was filtered and washed well with water and then with ethanol and finally with ether to give the (R)-(–) 2-butyl mono ester of Catalyst A (0.5 g)

Solid State $^{31}$P nmr—MAS $\delta_P$ 31.25; $^{13}$C MAS $\delta_C$ 80.1, 65.4, 34-6, 34.14, 24.48, 13.05

EXAMPLE 31

A mixture of 2,3-dimethyl 2,3-butanediol (6.0 g) and catalyst A (0.1 g) was warmed with stirring to 150° C. for 12 h under a reflux condenser. The reaction flask was then set for distillation containing a small fractionating column and 3,3 dimethyl 2-butanone (4.9 g) was obtained as a colourless liquid in 83% yield. B.p. 106° C., Lit. b.p. 106° C.

Repeating this reaction with Catalysts B–K gave the ketone in similar yields.

EXAMPLE 32

Addition of 2,3-dimethyl 2,3-butanediol (6.0 g) to the distillation residue from Example 31 and repeating the procedure gave 3,3 dimethyl 2-butanone (4.9 g) as a colourless liquid in identical yield. B.p. 106° C., Lit. B.p. 106° C. No apparent reduction was observed in catalyst efficiency over many runs.

EXAMPLE 33

The catalyst residue from Example 31 was washed with acetone and methanol and then dried at 100° C. for 24 h at 1 mm of Hg. No apparent loss of activity was observed when Example 31 was repeated using this catalyst.

EXAMPLE 34

A mixture of 2,3-butandione mono oxime (2.0 g) and Catalyst C (0.1 g) was heated at 140° C. under a reflux condenser. Reaction was immediate and heating was continued for 10 h to give acetic acid and acetonitrile in quantitative yield.

EXAMPLE 35

A mixture of benzaldehyde (2.12 g, 20 mmol), Catalyst A or B (0.1 g) and pre-dried molecular sieves (2.0 g) in methanol (10 ml) was stirred at ambient temperature for 10 h. After filtration the solution was concentrated under reduced pressure to leave 1,1-diethoxy phenyimethane (3.0 g) as a white solid in 98% yield. A $^1$H nmr spectrum of the liquid indicated that the reaction had gone to completion.

$\delta_H$ 3.32 (6H, s, O$\underline{CH}_3$)

Repeating this reaction with the Catalysts C–U gave 1,1-dimethoxy phenylmethane in virtually quantitative yield.

EXAMPLE 36

A mixture of acetophenone (4.8 g, 40 mmol), ethylene glycol (6 ml) and Catalyst A (0.4 g) in toluene (30 ml) was refluxed under a Dean and Stark condenser for 4 h. The reaction mixture was cooled, filtered and washed with water (3×50 ml) and then dried over magnesium sulphate. On concentration 1-methyl-1-phenyl 1,3 dioxolane was obtained as a solid (6.0 g) in 93% yield.

M.p. 61° C.; lit. 61–62° C.

Repeating this reaction with Catalysts B–U gave the ketone in similar yields, though catalysts H, L, P and R required longer reaction times.

EXAMPLE 37

A mixture of acetophenone (2.4 g, 20 mmol), benzaldehyde (2.12 g, 20 mmol) and Catalyst A or B (0.8 g) in toluene (20 ml) was refluxed for 30 h under a Dean and Stark apparatus. After cooling, ether (100 ml) was added and the catalyst was filtered off and the filtrate concentrated under reduced pressure to give an oily solid. On re-crystallisation from hexane—ethyl acetate 1,3-diphenyl prop-2-en-1-one was obtained as colourless crystals (3.9 g) in 94% yield.

M.p. 60° C.; lit. 58–62° C.

EXAMPLE 38

A mixture of 1-octene (6.0 g) and Catalyst A or B (0.2 g) was refluxed with stirring under an atmosphere of nitrogen gas. After 24 h a $^1$H nmr spectrum was run on a sample taken from the reaction mixture. The spectrum indicated the presence of 1-octene and the rearranged product trans 2-octene.

EXAMPLE 39

A mixture of 1-phenyl-1-propanol (0.16 g, 1.17 mmol) and Catalyst A or B (30 mg) in toluene (1 ml) was stirred and heated at 75° C. for 10 h under nitrogen. Ether (20 ml) was added and the mixture was filtered to remove the catalyst. The organic washings were concentrated under reduced pressure at room temperature to afford β-methyl styrene as a colourless oil (0.13 g, 92%).

$\delta_H$ 7.47–7.1 (5H, m), 6.4 (1H, d, J 12 Hz), 6.25 (1H, dq, $J_1$ 12 Hz, $J_2$ 6 Hz) and 1.87 (3H, d, J6 Hz).

The filtered catalyst above was added to 1-phenyl-1-propanol (0.16 g) in toluene (1 ml). The same procedure as above was followed to afford β-methyl styrene as a colourless oil (0.13 g, 92%).

Repeating this reaction with catalysts C, D, E, F, and J gave β-methyl styrene in yields of >90%.

EXAMPLE 40

A mixture containing Catalyst A (0.05 g) and oleic acid (1.41 g, 5 mmol) and ethanol (10 ml) was refluxed with stirring for 40 h. On cooling ether (30 ml) was added and the catalyst was filtered off. The organic washings were combined and concentrated to give ethyl oleate as an oil (1.39 g, 90% yield).

$\delta_H$ 5.33 (2H, m, olefin hydrogens), 4.11 (2H, q, J 8 Hz, O$\underline{CH}_2$), 2.29(2H, t, J 9 Hz, $\underline{CH}_2$CO)

The filtered catalyst was added to oleic acid (1.41 g, 5 mmol) and ethanol (10 ml) and the procedure, above, was repeated. No loss in catalytic activity was observed and ethyl oleate (1.39 g, 90% yield) was obtained.

The reaction was repeated with Catalysts B, C and S in yields of respectively 91%, 92%, and 82%.

EXAMPLE 41

A mixture containing Catalyst A or B (0.05 g) and ethyl oleate (1.55 g, 5 mmol) and pentanol (10 ml) was refluxed with stirring for 40 h. On cooling ether (30 ml) was added and the catalyst was filtered off. The organic washings were combined and concentrated to give pentyl oleate as an oil (1.6 g, 91% yield).

$\delta_H$ 5.33 (2H, m, olefin hydrogens), 4.01 (2H, t, J 8 Hz, O$\underline{CH}_2$), 2.27(2H, t, J 9 Hz, $\underline{CH}_2$CO)

EXAMPLE 42

A mixture of acetophenone ketal (1.04 g, 6.3 mmol) and Catalyst A (0.07 g) was stirred in acetonitrile:water (1:1, 16 ml) at 80° C. for 2 h. On cooling to room temperature, the catalyst was filtered and washed with ethyl acetate (70 ml). The combined organic washings were washed with water, dried over magnesium sulphate, concentrated to give acetophenone as an oil (0.7 g, 92%).

$\delta_H$ 2.58 (3H, CO$\underline{CH}_3$, s)

The filtered catalyst A was added to acetophenone ketal (1.04 g, 6.3 mmol) in acetonitrile:water (1:1, 16 ml) and the above procedure was repeated to give acetophenone as a colourless oil (0.7 g, 92%).

Reaction was conducted with the same catalyst on four further occasions without any apparent loss of activity.

The reaction was repeated with Catalysts B, C, O, P, Q, R, T and U in yields of respectively 91%, 92%, 92%, 93%, 96%, 95%, 93% and 92%.

EXAMPLE 43

An organopolysiloxane phosphonic acid—Catalyst A-(2.0 g) was suspended in de-ionised water (20 ml) and the pH of the mixture was adjusted to pH 8 with dilute sodium hydroxide. A clear solution was obtained and the solution was made up to 50 ml with distilled and de-ionised water. To a sample of this solution (10 ml) was added cobalt nitrate hexahydrate (0.6 g) dissolved in de-ionised water (8 ml). The precipitate was filtered off to give the cobalt derivative of a organopolysiloxane phosphonic acid as a blue-purple solid (0.5 g).

The above was repeated using cobalt acetate tetrahydrate in place of cobalt nitrate and afforded a blue solid (0.48 g)

EXAMPLE 44

An organopolysiloxane phosphonic acid—Catalyst B-(2.0 g) was suspended in de-ionised water (20 ml) and the pH of the mixture was adjusted to pH 8 with dilute sodium hydroxide. A clear solution was obtained and the solution was made up to 50 ml with distilled and de-ionised water. To a sample of this solution (10 ml) was added chromium nitrate nonahydrate (0.6 g) dissolved in de-ionised water (18 ml). The precipitate was filtered off to give the chromium derivative of a organopolysiloxane phosphonic acid as a deep purple solid (0.5 g).

EXAMPLE 45

Sodium hydroxide (1M) was added slowly over 2 h to a mixture of Catalyst A (0.2 g) in water (20 ml) to reach at pH of 9. The mixture was concentrated under reduced pressure and then washed with ethanol and finally with ether to give the di sodium salt as a white solid (0.2 g).
Solid State $^{31}$P nmr-MAS $\delta_P$ 27.25
$^{13}$C (D$_2$O) $\delta_C$ 21.1 SiCH, 31.0 SiCH$\underline{CH}_2$P $^1$H D$_2$O) $\delta_H$ 0.99 SiCH and 1.63 and 1.27 SiCH$\underline{CH}_2$P.
$^{13}$C (D$_2$O) $\delta_C$ 22.6 SiCH$_2\underline{CH}_2$P and $\delta_H$ 1.36 SiCH$_2\underline{CH}_2$P.

EXAMPLE 46

Lithium hydroxide (1M) was added slowly over 2 h to a mixture of Catalyst B (0.2 g) in water (20 ml) to reach at pH of 9. The mixture was concentrated under reduced pressure and then washed with ethanol and finally with ether to give the dilithium salt as a white solid (0.2 g).
Solid State $^{31}$P nmr-MAS $\delta_P$ 28.52

EXAMPLE 47

Sodium hydroxide (1M) was added slowly over 2 h to a mixture of Catalyst B (1.2 g) in water (20 ml) to reach at pH of 9. An aqueous solution of ammonium cerium nitrate (1.05 g) in water (20 ml) was added to give a yellow solid. The solid was filtered, washed well with deionised water and then with ethanol and finally with ether. A yellow solid (1.45 g) was obtained.

EXAMPLE 48

Sodium hydroxide (1M) was added slowly over 2 h to a mixture of Catalyst B (0.6 g) in water (20 ml) to reach at pH of 9. An aqueous solution of vanadium sulphate (0.6 g) in water (20 ml) was added to give a blue green solid. The solid was filtered, washed well with deionised water and then with ethanol and finally with ether. A blue grey solid (0.74 g) was obtained.

EXAMPLE 49

Sodium hydroxide (1M) was added slowly over 2 h to a mixture of Catalyst B (0.6 g) in water (20 ml) to reach at pH of 9. An aqueous solution of nickel nitrate (0.6 g) in water (20 ml) was added to give a blue green solid. The solid was filtered, washed well with deionised water and then with ethanol and finally with ether. A blue solid (0.78 g) was obtained.

EXAMPLE 50

Sodium hydroxide (1M) was added slowly over 2 h to a mixture of Catalyst B (0.6 g) in water (20 ml) to reach at pH of 9. An aqueous solution of cupric nitrate (0.6 g) in water (20 ml) was added to give a blue green solid. The solid was filtered, washed well with deionised water and then with ethanol and finally with ether. A pale blue solid (0.71 g) was obtained.

EXAMPLE 51

Hydrogen peroxide (30%, 2 ml) was added to a mixture of the catalyst from Example 48 (0.04 g) and cis-cyclooctene (1.4 g, 11.5 mmol) in tert-butanol (10 ml) at 30° C. under an atmosphere of nitrogen. The reaction mixture was stirred at 30° C. for 48 h under nitrogen. The catalyst was filtered off and washed well with ether (80 ml). The combined organic layers were washed well with water (2×40 ml) and then dried over magnesium sulphate. After filtration the solvent was removed under reduced pressure −20° C. at 50 mm of Hg—to afford 9-oxabicyclo[6.1.0] nonane as a white solid (0.95 g, 65%). M.p. 51° C., lit. m.p. 53–56° C.

EXAMPLE 52

A mixture of the Ce$^{iv}$ catalyst from EXAMPLE 47 (0.08 g), sodium bromate (0.3 g) and 4-fluorobenzyl alcohol (0.256 g, 2 mmol) in acetonitrile:water (1:1, 10 ml) was stirred at 80° C. for 40 h under an atmosphere of nitrogen. On cooling ether (70 ml) was added and the catalyst was filtered off. The organic layer was separated and the aqueous phase was extracted with ether (2×50 ml). The combined organic extracts were washed with water (25 ml), dried with anhydrous magnesium sulphate and concentrated to give 4-fluorobenzoic acid as a white solid (0.24 g, 86%). M.p. 182° C., lit. 185° C.

The separated catalyst was added to a fresh batch of sodium bromate (0.3 g) and 4-fluorobenzyl alcohol (0.256 g, 2 mmol) in acetonitrile:water (1:1, 10 ml). The above procedure was repeated to give 4-fluorobenzoic acid as a white solid (0.25 g, 88%).

EXAMPLE 53

A mixture of Ce$^{iv}$ catalyst from EXAMPLE 47 (0.08 g), sodium bromate (0.3 g) and benzyl alcohol (0.216 g, 2 mmol) in acetonitrile:water (5:7, 12 ml) was stirred at 80° C. for 40 h under an atmosphere of nitrogen. On cooling ether (70 ml) was added and the catalyst was filtered off. The organic layer was separated and the aqueous phase was extracted with ether (2×50 ml). The combined organic extracts were washed with water (25 ml), dried with anhydrous magnesium sulphate and concentrated to give benzoic acid as a white solid (0.22 g, 90%). M.p. 120° C., lit. 120–122° C.

The separated catalyst was added to a fresh batch of sodium bromate (0.3 g) and benzyl alcohol (0.216 g, 2 mmol) in acetonitrile:water (5:7, 12 ml). The above procedure was repeated to give benzoic acid as a white solid (0.22 g, 90%).

The separated catalyst was added to a fresh batch of sodium bromate (0.3 g) and benzyl alcohol (0.216 g, 2 mmol) in acetonitrile:water (5:7, 12 ml). The above procedure was repeated to give benzoic acid as a white solid (0.21 g, 87%).

EXAMPLE 54

A mixture of Ce$^{iv}$ catalyst from EXAMPLE 47 (0.08 g), sodium bromate (0.3 g) and 4-methylbenzyl alcohol (0.24 g, 2 mmol) in acetonitrile:water (1:1, 10 ml) was stirred at 80° C. for 40 h under an atmosphere of nitrogen. On cooling ether (70 ml) was added and the catalyst was filtered off. The organic layer was separated and the aqueous phase was extracted with ether (2×50 ml). The combined organic extracts were washed with water (25 ml), dried with anhydrous magnesium sulphate and concentrated to give 4-methylbenzoic acid as a white solid (0.26 g, 96%). M.p. 178° C., lit. 180–182° C.

EXAMPLE 55

To a mixture under nitrogen containing 5-pregnene-3β-acetoxy-20-one (0.716 g, 2 mmol) and the cobalt catalyst from Example 43 (70 mg) in acetonitrile (15 ml) was added tert-butyl hydroperoxide (5M in decane, 2.4 ml). The reaction mixture was warmed to 50–60° C. and stirred for 24 h. On cooling the reaction mixture was poured onto water (25 ml) and extracted into ethyl acetate (4×25 ml). The combined organic extract was washed with bicarbonate solution and with brine and then dried over magnesium sulphate. On concentration the residue was eluted from a flash silica column with ethyl acetate—pet. ether to give the 5-ene-7-one derivative in 70% yield.

EXAMPLE 56

An organopolysiloxane phosphonic acid—Catalyst A or B-(2.0 g) was suspended in de-ionised water (20 ml) and the pH of the mixture was adjusted to pH 8 with dilute sodium hydroxide. A clear solution was obtained and the solution was made up to 50 ml with distilled and de-ionised water. To a sample of this solution (2 ml) was added de-ionised water (2 ml) and a known concentration of a solution (2 ml) of a metal salt. The resultant mixtures were centrifuged to remove the precipitate and known spectroscopic and/or analytical methods were used to analyse the concentration of the metal remaining in the solution.

The disclosures of each patent, patent application and publication cited or described in this document are hereby incorporated herein by reference, in their entirety.

For example a sample of cobalt nitrate hexahydrate (1.433 M, 2 ml) was added to a sample of the organopolysiloxane phosphonic acid solution (2 ml), above, and de-ionised water (2 ml). The resultant mixtures were centrifuged to remove the precipitate and a UV spectrum was run on the remaining liquid. Comparison of the, intensity of the peak at 511 nm with a standard solution of cobalt nitrate hexahydrate indicated that 0.08 g of this organopolysiloxane phosphonic acid can abstract 0.018 g of $Co^{+2}$ metal.

The invention claimed is:
1. A compound of General Formula 1:

wherein R and $R^1$ are each independently hydrogen, a linear or branched $C_{1-40}$ alkyl, $C_{2-40}$ alkenyl or $C_{2-40}$ alkynyl group, an aryl or $C_{1-40}$ alkylaryl group or an optionally complex metal ion $M^{n+}/n$ wherein n is an integer from 1 to 8;

the free valences of the silicate oxygen atoms are saturated by one or more of:

silicon atoms of other groups of Formula 1, hydrogen, a linear or branched $C_{1-12}$ alkyl group or by cross-linking bridge members $R^3_q M^1(OR^2)_m O_{k/2}$ or $Al(OR^2)_{3-p} O_{p/2}$ or $R^3 Al(OR^2)_{2-r} O_{r/2}$;

where $M^1$ is Si or Ti;

$R^2$ is a linear or branched $C_{1-12}$ alkyl group; and $R^3$ is a linear or branched $C_{1-16}$ alkyl group;

k is an integer from 1 to 4 and q and m are integers from 0 to 2;

such that m+k+q=4; and p is an integer from 1 to 3; and r is an integer from 1 to 2;

or other known oxo metal bridging systems;

x, y and z are integers such that the ratio of x:y+z, varies from 0.00001 to 100,000 with the fragments $[O_{3/2}SiCH(CH_2PO(OR^1)(OR^1))CH_2CH_2SiO_{3/2}]_x$ and $[O_{3/2}SiCH_2CH_2PO(OR)(OR^1)]_y$ always present whilst the integer z various from 0 to 200y.

2. The compound as claimed in claim 1, comprising a cross linking bridge member and wherein the ratio of cross linker to x+y+z varies from 0 to 99:1.

3. The compound as claimed claim 1, comprising a cross linking bridge member derived from an orthosilicate, a titanium alkoxide or an aluminum trialkoxide.

4. The compound as claimed in claim 1, comprising a cross linking bridge member selected from the group consisting of $SiO_{4/2}$, $R^3 SiO_{3/2}$, $(R^3)_2 SiO_{2/2}$, $TiO_{4/2}$, $R^3 TiO_{3/2}$, $(R^3)_2 TiO_{2/2}$, $AlO_{3/2}$ and $R^3 AlO_{2/2}$, wherein $R^3$ is a linear or branched $C_{1-6}$ alkyl group.

5. The compound as claimed in claim 4 wherein $R^3$ is $C_{1-4}$ alkyl.

6. The compound as claimed in claim 1, wherein R and $R^1$ are each independently hydrogen, $C_{1-12}$ alkyl, $C_{2-12}$ alkenyl, $C_{2-12}$ alkynyl, aryl or $C_{1-8}$ alkylaryl.

7. The compound as claimed in claim 1, wherein R and $R^1$ are each independently hydrogen, $C_{1-4}$ alkyl, phenyl or $C_{1-8}$ alkylaryl.

8. The compound as claimed in claim 1, wherein R and $R^1$ are each independently hydrogen, methyl, ethyl or phenyl.

9. The compound as claimed in claim 1, wherein either or both of R and $R^1$ is hydrogen.

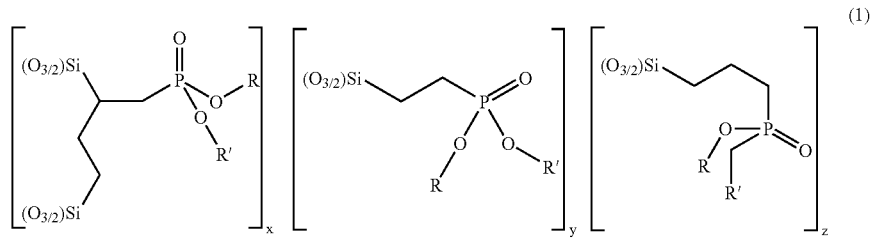

10. The compound as claimed in claim 1, wherein one of R and $R^1$ is hydrogen and the other is $C_{1-40}$ alkyl, $C_{2-40}$ alkenyl, $C_{2-10}$ alkynyl, aryl, $C_{1-8}$ alkylaryl or a metal ion derived from a lanthanide, actinide, main group or transition metal.

11. The compound as claimed in claim 1, wherein one of R or $R^1$ is hydrogen and the other is $C_{1-4}$ alkyl, phenyl, or $C_{1-8}$ alkylaryl.

12. The compound as claimed in claim 1, wherein one of R or $R^1$ is hydrogen or $M^{n+}/n$ and the other is $C_{12-40}$ alkyl, $C_{12-40}$ alkenyl, $C_{12-40}$ alkynyl, $C_{12-40}$ alkylaryl or aryl.

13. The compound as claimed in claim 1, wherein either or both of R and $R^1$ is $M^{n+}/n$.

14. The compound as claimed in claim 1, wherein one of R and $R^1$ is $M^{n+}/n$ and the other is hydrogen or a $C_{1-12}$ alkyl, $C_{1-12}$ alkenyl, $C_{1-12}$ alkynyl, aryl or $C_{1-12}$ alkylaryl group.

15. The compound as claimed in claim 1, wherein one or both of R and $R^1$ is $M^{n+}/n$, and $M^{n+}$ is derived from a lanthanide, actinide, main group or transition metal.

16. The compound as claimed in claim 15, wherein $M^{n+}$ is derived from a lanthanide, main group or transition metal.

17. A process for the preparation of a compound of Formula 1 as defined in claim 1, in which R and $R^1$ are each independently $C_{1-12}$ alkyl, alkylaryl or aryl, the process comprising:
  i. conducting a free radical addition reaction of a dialkyl or diaryl phosphite of Formula VI:

$$P(OR)_2OH \quad (VI)$$

where R is $C_{1-12}$ alkyl, aryl or $C_{1-12}$ alkylaryl;
  to trialkoxy vinyl silane of Formula V:

$$H_2C=CHSi(OR^4)_3 \quad (V)$$

where $R^4$ is $C_{1-12}$ alkyl, aryl or $C_{1-12}$ alkylaryl;
  in the presence of a free radical initiator and under an atmosphere of nitrogen to give a mixture of compounds of Formulae II and IV:

$$(R^4O)_3SiCH_2CH_2PO(OR)(OR^1) \quad (II)$$

$$(R^4O)_3SiCH(CH_2PO(OR)(OR^1))CH_2CH_2Si(OR^4)_3 \quad (IV)$$

wherein R, $R^1$ and $R^4$ are $C_{1-12}$ alkyl, alkylaryl or aryl, preferably a methyl or ethyl group;
  ii. combining, in the desired ratios, compounds of Formulae II, III and IV, where R, $R^1$ and $R^4$ are $C_{1-12}$ alkyl, alkylaryl or aryl:

$$(R^4O)_3SiCH_2CH_2CH_2PO(OR)(OR^1) \quad (III)$$

iii. hydrolysing the mixture under acid or basic conditions; and optionally
  iv. adding a cross linking bridging precursor compound in a required quantity.

18. A process for the preparation of a compound of Formula 1 as defined in claim 1, in which R and $R^1$ are both hydrogen, and z=0, the process comprising:
  i. conducting a free radical addition reaction between phosphorous acid of formula $H_3PO_3$ and a vinyl trialkoxysilane of Formula V:

$$H_2C=CHSi(OR^4)_3 \quad (V)$$

where $R^4$ is $C_{1-12}$ alkyl, aryl or $C_{1-12}$ alkylaryl; and optionally
  ii. adding a cross linking bridging precursor compound in a required quantity.

19. A process for the preparation of a compound of Formula 1 as defined in claim 1, in which R is hydrogen and $R^1$ is $C_{1-12}$ alkyl, alkylaryl or aryl, the process comprising hydrolysing a compound of Formula 1 in which both R and $R^1$ are $C_{1-12}$ alkyl, alkylaryl or aryl under dilute acid or basic conditions.

20. A process for the preparation of a compound of Formula 1 as defined in claim 1, in which R is hydrogen and $R^1$ is $C_{1-40}$ alkyl, $C_{2-40}$ alkenyl, $C_{2-40}$ alkynyl, aryl or $C_{1-40}$ alkylaryl, the process comprising treating a compound of Formula 1 in which both R and $R^1$ are hydrogen with an acid chloride, concentrating the mixture, and then reacting with a required alcohol $R^1OH$.

21. A process for the preparation of a compound of Formula 1 as defined in claim 1, in which R and $R^1$ are both hydrogen, the process comprising hydrolysing a compound of Formula 1 in which both R and $R^1$ are $C_{1-12}$ alkyl, alkylaryl or aryl in concentrated acid.

22. A process for the preparation of a compound of Formula 1 as defined in claim 1, in which R and/or $R^1$ is $M^{n+}/n$, the process comprising reacting a compound of Formula 1 in which R and/or $R^1$ is hydrogen with base, and then adding a solution containing the desired metal ion and/or complex.

23. The process as claimed in claim 17, further comprising combining a precursor to a cross linking bridge member with the desired amounts of the compounds of Formulae II, III and IV.

24. The process as claimed in claim 18, further comprising adding a precursor to a cross linking bridge member to the free radical reaction.

25. The process as claimed in claim 23, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO2/2$, where $R^3$ is a linear or branched $C_{1-6}$ alkyl group.

26. The process as claimed in claim 24, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is a linear or branched $C_{1-6}$ alkyl group.

27. The process as claimed in claim 17, further comprising combining a template to aid the preparation of pores with particular sizes and distributions in compounds of Formula 1 with the desired amounts of the compounds of Formulae II, III and IV, and then removing the template from the compound of Formula 1 by washing.

28. The process as claimed in claim 18, further comprising adding a template to aid the preparation of pores with particular sizes and distributions in compounds of Formula 1 to the free radical reaction, and then removing the template from the compound of Formula 1 by washing.

29. The anti-microbial agent composition comprising a compound as claimed in claim 9.

30. The anti-microbial agent composition comprising a compound as claimed in claim 10.

31. The anti-microbial agent composition comprising a compound as claimed in claim 12.

32. The anti-microbial agent composition comprising a compound as claimed in claim 13.

33. The anti-microbial agent composition comprising a compound as claimed in claim 14.

34. The anti-microbial agent composition comprising a compound as claimed in claim 15.

35. The process as claimed in claim 18, further comprising combining a precursor to a cross linking bridge member with the desired amounts of the compounds of Formulae II, III and IV.

36. The process as claimed in claim 19, further comprising combining a precursor to a cross linking bridge member with the desired amounts of the compounds of Formulae II, III and IV.

37. The process as claimed in claim 20, further comprising combining a precursor to a cross linking bridge member with the desired amounts of the compounds of Formulae II, III and IV.

38. The process as claimed in claim 21, further comprising combining a precursor to a cross linking bridge member with the desired amounts of the compounds of Formulae II, III and IV.

39. The process as claimed in claim 22, further comprising combining a precursor to a cross linking bridge member with the desired amounts of the compounds of Formulae II, III and IV.

40. The process as claimed in claim 35, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is a linear or branched $C_{1-6}$ alkyl group.

41. The process as claimed in claim 36, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is a linear or branched $C_{1-6}$ alkyl group.

42. The process as claimed in claim 37, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is a linear or branched $C_{1-6}$ alkyl group.

43. The process as claimed in claim 38, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is a linear or branched $C_{1-6}$ alkyl group.

44. The process as claimed in claim 39, wherein the cross-linking bridge member is $SiO_{4/2}$ or $R^3SiO_{3/2}$ or $(R^3)_2SiO_{2/2}$ or $TiO_{4/2}$ or $R^3TiO_{3/2}$ or $(R^3)_2TiO_{2/2}$ or $AlO_{3/2}$ or $R^3AlO_{2/2}$, where $R^3$ is a linear or branched $C_{1-6}$ alkyl group.

45. The process as claimed in claim 18, further comprising combining a template to aid the preparation of pores with particular sizes and distributions in compounds of Formula 1 with the desired amounts of the compounds of Formulae II, III and IV, and then removing the template from the compound of Formula 1 by washing.

46. The process as claimed in claim 19, further comprising combining a template to aid the preparation of pores with particular sizes and distributions in compounds of Formula 1 with the desired amounts of the compounds of Formulae II, III and IV, and then removing the template from the compound of Formula 1 by washing.

47. The process as claimed in claim 20, further comprising combining a template to aid the preparation of pores with particular sizes and distributions in compounds of Formula 1 with the desired amounts of the compounds of Formulae II, III and IV, and then removing the template from the compound of Formula 1 by washing.

48. The process as claimed in claim 21, further comprising combining a template to aid the preparation of pores with particular sizes and distributions in compounds of Formula 1 with the desired amounts of the compounds of Formulae II, III and IV, and then removing the template from the compound of Formula 1 by washing.

49. The process as claimed in claim 22, further comprising combining a template to aid the preparation of pores with particular sizes and distributions in compounds of Formula 1 with the desired amounts of the compounds of Formulae II, III and IV, and then removing the template from the compound of Formula 1 by washing.

* * * * *